United States Patent [19]

Mills

[11] Patent Number: 4,803,435

[45] Date of Patent: Feb. 7, 1989

[54] METHOD AND APPARATUS FOR DETECTING DIELECTRIC DEFECTS

[75] Inventor: Louis T. Mills, Loveland, Colo.

[73] Assignee: Hewlett-Packard Company, Palo Alto, Calif.

[21] Appl. No.: 920,104

[22] Filed: Oct. 16, 1986

[51] Int. Cl.$^4$ ............................................. G01N 27/60
[52] U.S. Cl. ..................................... 324/456; 324/452
[58] Field of Search ............... 324/452, 454, 455, 456, 324/438, 439, 557, 551, 558, 554, 71.5, 73 PC; 204/1 T

[56] References Cited

U.S. PATENT DOCUMENTS

| | | | |
|---|---|---|---|
| 2,499,467 | 3/1950 | De Forest et al. | 324/456 |
| 2,669,692 | 2/1954 | Pearson | 324/456 X |
| 2,678,420 | 5/1954 | De Forest et al. | 324/456 |
| 3,234,462 | 2/1966 | Holdsworth | 324/452 X |
| 4,251,775 | 2/1981 | Michel | 324/71.5 X |
| 4,443,764 | 4/1984 | Suh et al. | 324/456 |
| 4,463,316 | 7/1984 | Messins et al. | 324/453 X |
| 4,578,279 | 3/1986 | Zingher | 324/73 PC |
| 4,668,916 | 5/1987 | Pech | 324/456 |

FOREIGN PATENT DOCUMENTS 1026088  6/1983  U.S.S.R. .............................. 324/456

Primary Examiner—M. H. Paschall
Assistant Examiner—A. Jonathan Wysocki
Attorney, Agent, or Firm—William W. Cochran

[57] ABSTRACT

Small and/or large defects in dielectric materials can be detected by bombarding one surface of the dielectric material with gas ions in order to impart a charge on that surface while the opposite surface is under the influence of an opposite charge. The dielectric material is then exposed to an indicator substance having an affinity for the charge of the gas ions and a tendency to congregate on regions of the dielectric materials which contain defects.

18 Claims, 8 Drawing Sheets

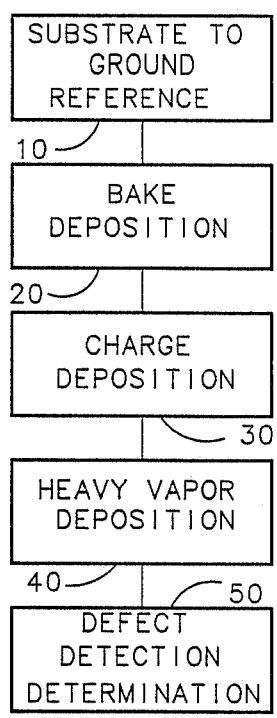
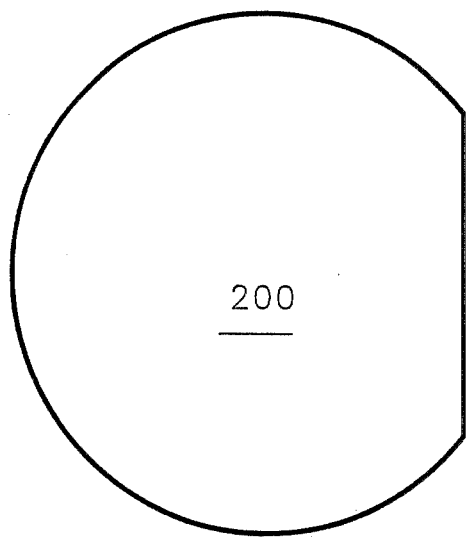
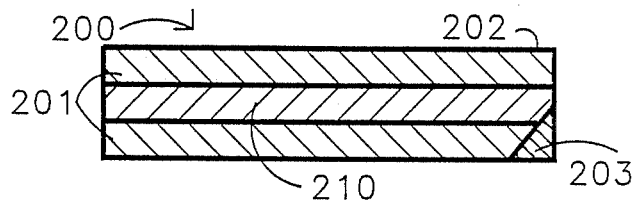
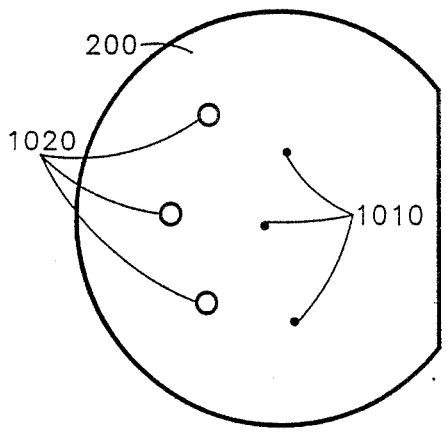

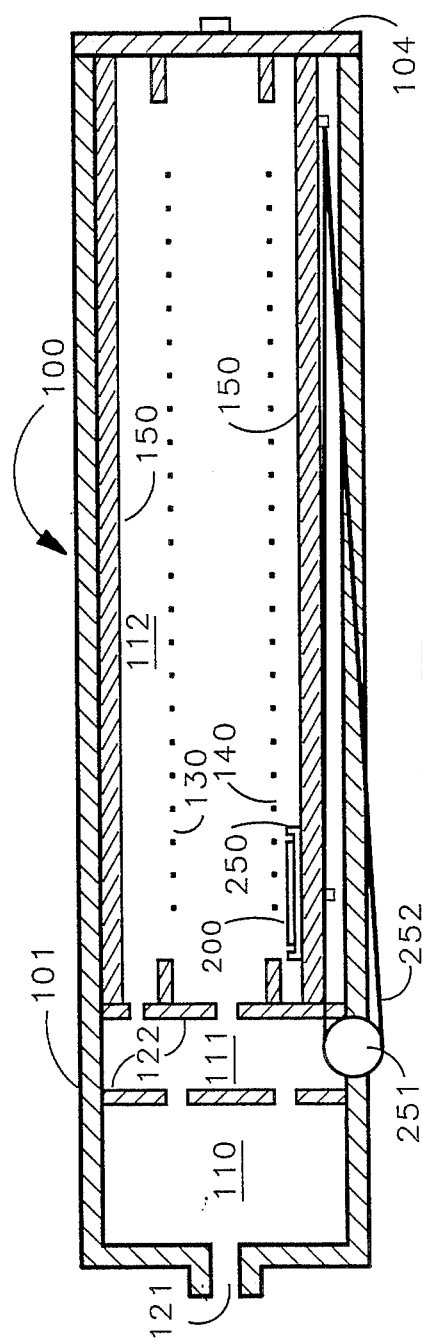

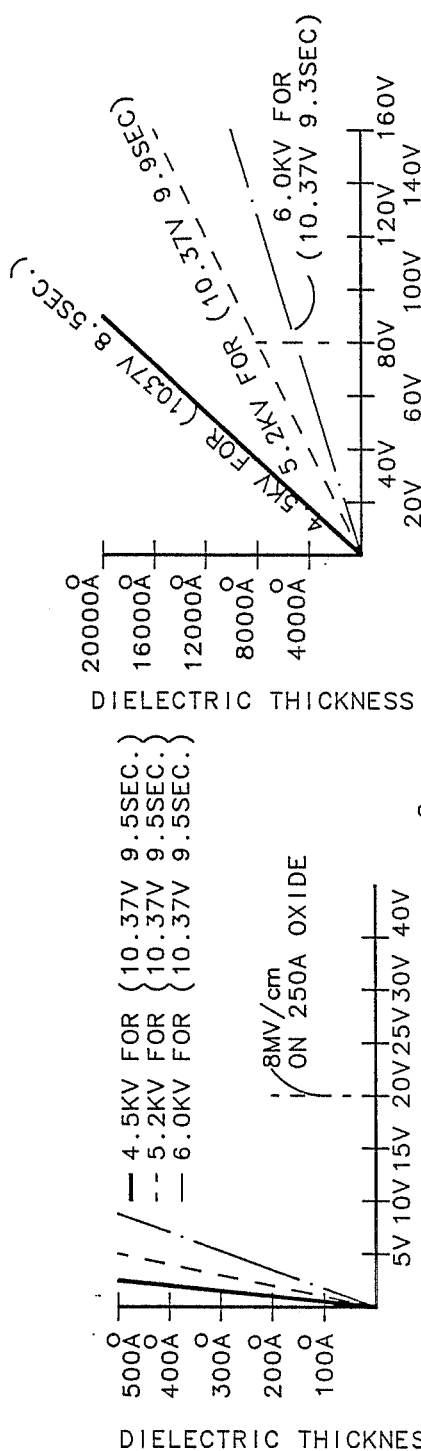
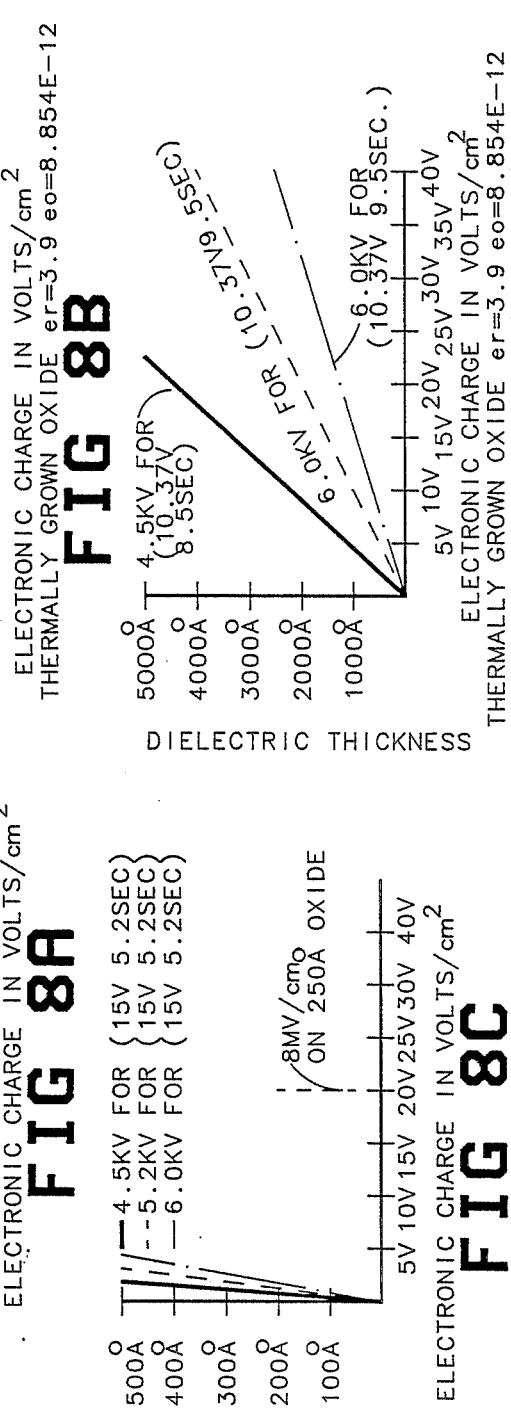

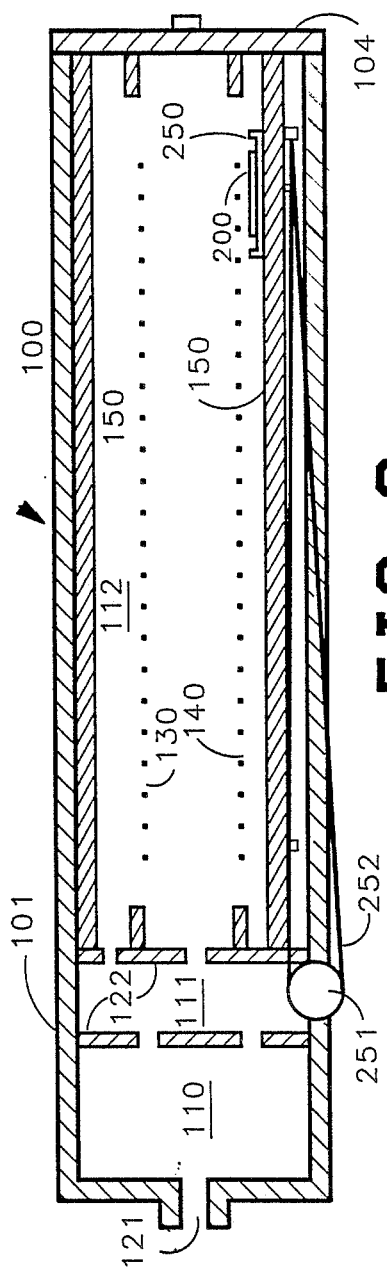

METHOD AND APPARATUS FOR DETECTING DIELECTRIC DEFECTS

BACKGROUND

1. Field of Invention

This invention relates to the field of defect detection in dielectric materials, and more particularly to a method and apparatus for discovering small defects in the silicon dioxide layers of integrated circuit devices. The invention is especially adapted to discovering defects with a diameter between 10 and 100,000 angstroms in a silicon dioxide ("oxide") layer of an integrated circuit, however, the invention is equally useful for detecting defects in any dielectric which can be located on a conductor.

2. Description of the Prior Art

Prior art detection techniques were limited to detecting only surface passivation defects. These techniques, generally referred to as reverse carbon decoration, deposit a thick carbon layer on the surface of the dielectric.

Reverse carbon deposition was a two step process. The first step of the process exposed the dielectric to a stationary electric field. A large charge was deposited on the surface of the dielectric to a potential of several hundred volts/cm$^2$. The second step of the process was to deposit an indicator on the surface of the dielectric. The carbon particles were attracted to the charge and left a thick layer of carbon on the surface of the dielectric. The dielectric was then examined for defects which were located where the carbon was not.

The prior art techniques has many problems. One serious problem is that the carbon layer obscured the veiw of the wafer making it difficult to locate the defects relative to the other circuitry located on the wafer. This severely complicates solving the problem. Prior art techniques also could not detect defects in varying oxide thicknesses since these variations could be mistaken as defects.

What is needed is a method and apparatus for detecting small and large defects in a dielectric which varies in thickness.

SUMMARY

In accordance with the preferred embodiment of the present invention, a method and apparatus are described for detecting small and large defects in dielectrics of varying thickness. Such defects are commonly found in metal oxide gate FET integrated circuits. The method comprises the steps of depositing a charge on the surface of the dielectric employing a nonstationary electric field and then depositing an indicator on the surface of the dielectric. Defects in the dielectric cause the charge being deposited to be concentrated in the area surrounding the defect. The center of this area, where the defect is located, will be highly charged for small defects or discharged for large defects. After the charge has been deposited, the indicator is deposited on the surface of the dielectric material. The indicator is attracted to the surface of the dielectric material by the charge. Where it contacts the charge, the indicator attaches to the dielectric material. In the preferred embodiment, the indicator contains carbon among other chemicals. Since the carbon is attracted to the charge, the defects are located where the carbon is heavily deposited. The defects typically form a ring or "taurus", or a point or "omega". Two apparatuses are disclosed, an ionization unit for depositing a charge on the surface of the dielectric matrerial and deposition unit for depositing the indicator on the surface of the dielectric material.

The primary object of the present invention, therefore, is to provide a method for detecting small and large defects in a dielectric material. Defects should be detected not only on the surface of thick and thin dielectric materials, but also on inner dielectric layers.

Another object of the present invention is to have a method which after a defect is detected, its position may be easily located relative to the circuitry on the integrated circuit.

A further object of the present invention is to have a method which is reliable and repeatable and which is compatible with integrated circuit manufacturing processes.

The present invention is superior to the prior art in many ways. First, the present invention is capable of detecting defects as small as 10 angstroms in diameter. Defects of any size may be detected even in very thin dielectrics having a thickness of only 30 to 40 angstroms. Second, the invention is capable of detecting defects on inner layers of an integrated circuit. Third, this invention is capable of detecting defects over the complete surface of the dielectric. The invention is capable of depositing charge with a resolution of less than .1 um and within 1 um of a large ground plane. Fourth, the invention is capable of depositing a very thin layer of carbon particles uniformly over the surface of the dielectric without artifacts such as evaporation rings. Finally, this method may be automated with its resulting reliability and repeatability.

DESCRIPTION OF DRAWINGS

FIG. 5 is a flowchart illustrating the preferred embodiment of the present invention.

FIG. 6A is a top view of a silicon wafer and FIG. 6B is a cross section view of a wafer having a dielectric layer.

FIG. 7 is a cross section view of an ionization unit in accordance with the preferred embodiment of the present invention with the wafer in the starting position.

FIG. 8A-D are graph of the high voltage and time required to deposit a charge of a particular potential on the surface of the dielectric.

FIG. 9 is a cross section view of an ionization unit in accordance with the preferred embodiment of the present invention with the wafer in the ending position.

FIG. 11 is the top view of a wafer following the defect detection process illustrating the types of defects found on such a wafer.

DESCRIPTION OF THE PREFERRED EMBODIMENT

A process in accordance with the present invention comprises the steps of depositing a charge on the surface of the dielectric employing a nonstationary electric field and then depositing an indicator on the surface of the dielectric to identify the location of the defect. An ionization unit is employed to deposit the charge on the surface of the dielectric. A deposition unit is employed to deposit an indicator on the surface of the dielectric.

Figure 1:
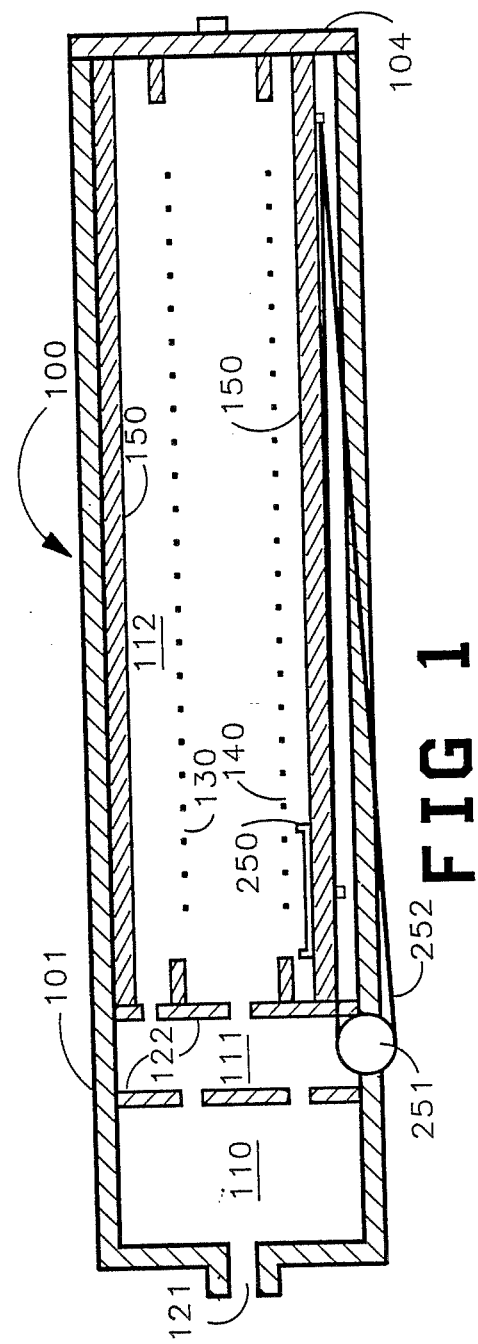
FIG. 1 is a cross section view of an ionization unit in accordance with the preferred embodiment of the present invention.

FIG. 1 is a cross section view of an ionization unit in accordance with the preferred embodiment of the present invention. The ionization unit 100 comprises a frame, ionization gas delivery system, ionization system and linear drive system. The frame comprises a box frame 101 with top, bottom, and left, front and right sides and a door 104. The ionization gas delivery system comprises intake port 121 in the box frame 101, and two baffle plates 122 which divide the unit into two manifold chambers 110 and 111 and an ionization chamber 112. The ionization system comprises an anode 130, a dual focusing grid 140, and two cathodes 150 located in the ionization chamber 112. The ionization system ionizes the ionization gas to form positive ions which bombard the dielectric material. As the positive ions hit the dielectric material, the ions transfer their charge to the surface of the dielectric material Nitrogen is employed as the ionization gas in the preferred embodiment of the present invention. The linear drive system comprises a wafer carrier 250, drive motor 251 and belt 252. The dielectric material under test is carried through the ionization chamber 112 between the cathode 150 and the dual focusing grid 140. These systems work together to deposit a uniform charge over the surface of the dielectric material.

The ionization unit operates as follows. The ionization gas distribution system delivery the ionization gas to the ionization chamber 112. The ionization gas is fed into the ionization unit through an intake port 121 in the side of box frame 101 and flows through the two manifold chambers into the ionization chamber 112 and then out door 104. In order to achieve uniform ionization, the gas must flow smoothly and evenly, referred to as a laminer flow, through the ionization chamber 112. In order to achieve a laminer flow in the preferred embodimnet, the gas is distributed through two manifold chambers 110 and 111 formed by the frame and two baffle plates 122. In the first manifold 110, the point concentration of the ionization gas coming through the input port 121 is dispersed into the full volume of the first manifold 110. In the second manifold 111, the flow is further conditioned by forcing the flow of ionization gas to form a laminar flow into the ionization chamber 112. This laminar flow of ionization gas progresses through the ionization chamber to the outside environment through uniformly spaced holes in the door 104. In the preferred embodiment, the nitrogen gas flows through the ionization unit at approximately 2 liters per minute.

The ionization system ionizes the ionization gas and delivers a uniform flow of positive ionization gas ions to the dielectric material located in the wafer carrier 250. The wafer carrier is located between the dual focusing grid 140 and the bottom cathode 150. The non-uniform electric field generated by the anode is controlled by the dual focusing grid and the linear drive in order to deposit a uniform charge on the surface of the dielectric.

Figure 2A:
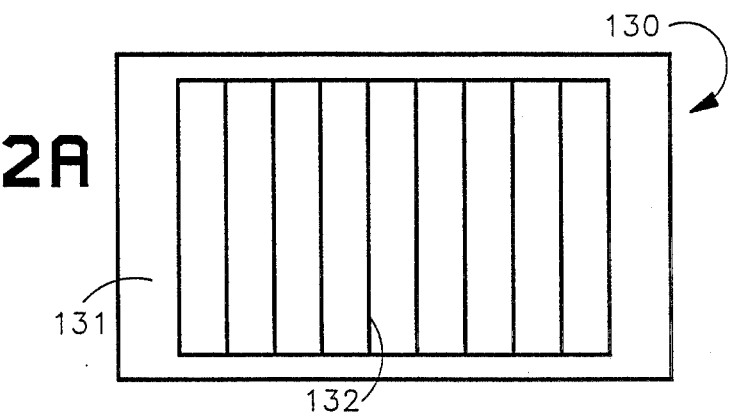
FIG. 2A is a top view of an anode and FIG. 2B is a side view of an anode.
Figure 2B:
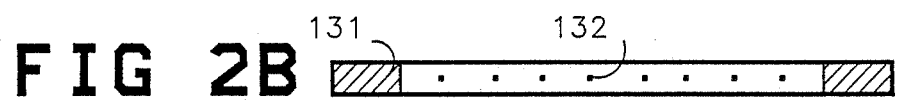

The nitrogen gas is first ionized by high potential placed between the anode 130 and to the cathode. 150. FIG. 2A is a top view of an anode and FIG. 2B is a side view of an anode. The anode comprises a frame 131 and anode wire 132. The anode wire 132 is made of 1 mil 303 stainless steel wire. The parallel anode wires are separated by approximately 1.2 cm. A small diameter wire is employed in the anode because it is capable of ionizing the nitrogen at normal atmospheric pressure at relative low voltages. The ionization starts at 3.6 KV and the ionization chamber may be operated through 7 KV with the anode 130 at positive potential relative to the cathode 150 which is referenced to ground. The cathode is made from aluminum which approximately 0.250 inches thick. The thickness accelerates the cooling of the pre-heated dielectrics. The cathode is placed above and below the anode to promote even flow of ions from the anode. The distance between the anode and the cathode may be adjusted for two reasons. First, the distance may be varied in order to adjust the charge connection. Second, the distance may be varied in order to accommodate thick dielectric materials. In the preferred embodiment of the present invention, the distance between the bottom cathode and the anode is approximately two and one-half centimeters.

Figure 3A:
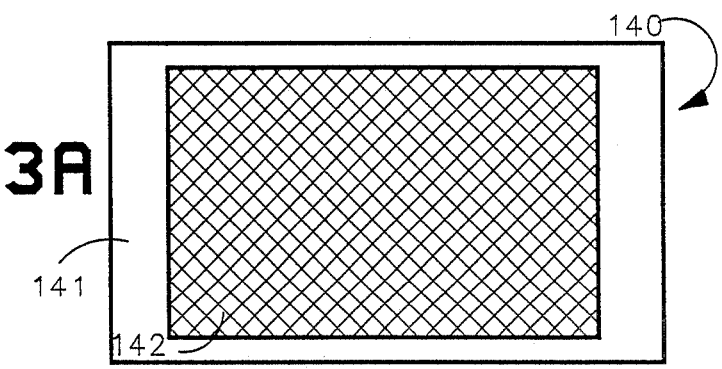
FIG. 3A is a top view and FIG. 3B is a side view of a dual focusing grid.
Figure 3B:
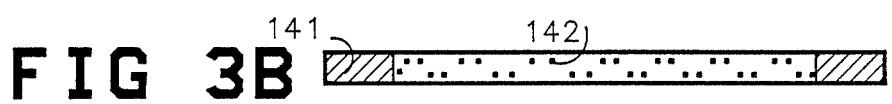

The resulting electric field between the anode and the cathode without the dual focusing grid is uneven because of the presence of the dielectric in close proximity to the cathode. The dual focusing grid is needed to compensate for the very small geometries and the close proximity between the cathode and the wafer. FIG. 3A is a top view and FIG. 3B is a side view of a dual focusing grid. The dual focusing grid comprises a frame 141 and two layers of grid wire 142. The two layers of cross-hatched grid wire are aligned so that the intersections of the first layer are approximately centered in the diamond shape area of the second layer and the layers are separated by approximately .050 inches. In the preferred embodiment, the dual focusing grid is, like the cathode, reference to ground potential. The grid may, however, by referenced to any small voltage above ground potential with equally satisfactory results. In the preferred embodiment, the dual focusing grid 140 is located approximately twenty in fifty mils above the dielectric when the dielectric is placed in wafer carrier 250. The grid operates by referencing the positive ions of gas to ground, thereby eliminating the effect of highly charged areas surrounding defects in the dielectric material. In the absence of the dual focusing grid, the positive ions would be affected by the charge already deposited on the surface of the dielectric which could cause the deposited charge to bloom into and over small geometry areas near the defect. The grid wire 142 is woven in small 45 degree diamond shaped segments which focus the charge and which when combined with the linear drive system below dratically reduce the phenomena of charge blooming and charge spreading. This insures that the dielectric material close to larger geometries of oxide and the cathode 150 will receive a charge which is proportional to its dielectric thickness.

The linear drive assembly ensures that a uniform charge is deposited on the surface of the dielectric material by moving the dielectric material at a constant velocity perpendicularly to the anode while the dielectricis being charged. The dielectric is placed in the wafer carrier 250 which is located between the bottom cathode 150 and teh dual focusing grid 140. The wafer carrier 250 is propelled along the cathode by the drive motor 251 and the belt 252. The wafer carrier is at ground potential by virtue of its contact with the cathode. The movement averages the small variations in charge caused by the small wire used in the anode and dual focusing grid to which each part of the dielectric material is exposed.

Figure 4:
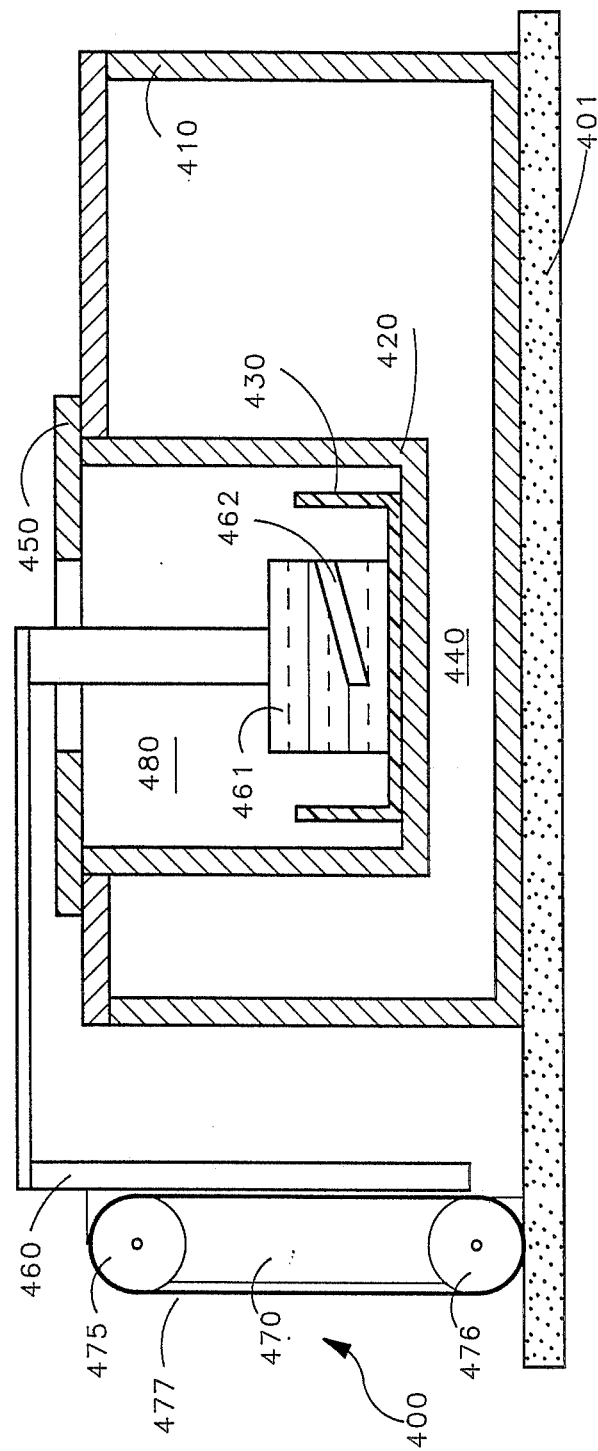
FIG. 4 is a cross section view of a heavy vapor deposition unit with the column positioning mechanism in the lower position.

FIG. 4 is a side view of a heavy vapor deposition unit. The heavy vapor deposition unit deposits the indicator on the surface of the dielectric material without disturbing the charge located on the surface of the dielectric material. The indicator is dissolved in a carrier. The dielectric material is placed in the indicator bath containing the indicator and the carrier. Where the indicator contacts the charge, the indicator attached to the dielectric material. The carrier is then allowed to evaporate in a control manner.

The deposition unit 400 comprises a base 401, a vapor canister, and a column lifting mechanism. The unit must deposit the indicator which is in a heavy vapor state in a reliable and repeatable manner. Therefore, the unit must control both the application of the indicator and the rate of deposition of the indicator by evaporation. There are two key aspects to this problem, the first aspect is maintaining the proper vapor pressure, and second is maintaining a controlled application.

The main parameter controlling vapor pressure is temperature. In order to maintain the appropriate vapor pressure, the indicator must be kept approximately zero degrees Celsius. An inexpensive long term cooling apparatus is motor driven freon refrigeration system. Glycol water is chilled by the freon refrigeration unit and then pumped up to the vapor canister.

In order to assure good repeatability in the application of the indicator, the dielectric has to be placed into the indicator bath the same way each and every time. The column lifting mechanism is incorporated into the heavy vapor deposition unit for this purpose. The column lifting mechanism comprises support 470 having a first and second wheel 475 and 476 mounted perpendicularly to the base 401 and a lift assembly. A belt 477 is attached to the wheels 475 and 476 and the lift assembly. The belt is driven by a motor (not shown) attached to drive wheel 476. The lift assembly is slidably attached to support 470. The lift assembly comprises a support 460 and a wafer carrier 461 having a slot 462 at approximately seven degrees from horizontal. The column lifting mechanism is controlled by microprocessor which drives the motor and senses the position of the lift assembly with microswitches.

The vapor canister comprises a stainless steel canister 410, a stainless steel vessel 420, a beaker 430 and a purge ring 450. The vessel 420 is mounted in the canister 410 forming the area 440. The area is filled with the chilled glycol water which is continuously circulated through the freon refrigeration system. In the preferred embodiment, the vessel 240 has a diameter of approximately seven and one half inches. A beaker 430 made of delrin is place at the bottom of the vessel and filled with the indicator bath. The purge ring 450 was designed to reduce the build up or accumulation of frost along the inside walls of the vessel. Dry nitrogen is pumped into the purge ring 450 where it flows into the top of the vessel and out the opening in the top of the vessel. The purge ring also retards the accumulation of dust on the indicator bath, by providing a flow of nitrogen up and outward blowing dust away from the opening in the vessel.

The indicator bath comprises FREON TF, carbon black, LUBRIZOL 894, ployethylene, and toluene. LUBRIZOL is available from Lubrizol Corp. In the preferred embodiment, the indicator is formed by mixing 17 gm of carbon black dissolved in 100 ml of Toluene with 10 ml of a solution of 50 gm of polyethylene dissolved in 50 ml of toluene and 10 ml of a solution of 50 mg of LUBRIZOL dissolved in 50 ml of toluene. 21 ml of the indicator is mixed with 3500 ml ofthe carrier, FREON TF, to provide a suitable indicator bath for heavy vapor deposition. The carbon black is available from Cities Services as RAVEN BLACK No. 1255 SL-3673. The polyethylene is available from Allied Chemical Model AC-430-polyethylene. After the Freon TF evaporates, the LUBRIZOL and polyethylene hold the carbon black particle in place to permit easier study of defects. Toluene is a solvent which allows the polyethylene and LUBRIZOL to mix with the carbon black. The carbon black must be dissolved completely in the solution without any clumps or clusters of carbon black.

FIG. 5 is a flowchart illustrating the preferred embodiment of the present invention for detecting defects in silicon dioxide dielectric layer on the surface of a silicon wafer. Such silicon wafers are typically employed in the manufacture of integrated circuits. The process consists of five steps labeled steps 10 through 50. Steps 10 through 30 correspond to the primary step of depositing a uniform charge on the surface of the dielectric material. Steps 40 and 50 correspond to the primary step of depositing an indicator on the surface of the dielectric material.

In order to place a uniform positive charge on the surface of the dielectric to be tested, a negative charge must be free to move around the opposite side of the dielectric material. Typically, the flow of negative charge is aided by a conductor or semiconductor located on the opposite side of the dielectric material. Therefore, the first step 10 of the process is to make a good electrical connection to the conductor located on the opposite side of the dielectric material. For a silicon wafer which has had oxide thermally grown on both side of the wafer, this means a good electrical connection must be made with the substrate. This may be easily achieved by grinding away the silicon dioxide on one of the wafer edges, preferably the flat edge and then painting the edge of the wafer with silver paint. The silver paint assures a good ground connection through the wafer carrier 250 to cathode 150.

The second sstep 20 of the process is to remove any water from the surface of the dielectric. Water, if present, would conduct the charge around the wafer destroying the defect detection capability. In the preferred embodiment of the present invention, water is removed by heating the wafer to approximately 150 degrees Celsius and then allowing the wafer to cool in a dry nitrogen environment of the ionization unit 100. The wafer is heated on a hot plate which is kept at 150 degrees Celsius. The wafer is then transferred to the ionization unit 100 where the wafer cools in a dry nitrogen environment, thereby preventing moisture from collecting again on the wafer. A static eliminator may be employed during steps 10 and 20 to reduce the buildup of static charge on the surface of the dielectric.

The thirds step 30 of the process is to deposit a uniform charge on the surface of the dielectric. In the preferred embodiment of the present inventio, the ionization unit 100 is employed to deposit the charge. The ionization unit 100 deposits the charge on the surface of the dielectric material by bombarding the surface with an ionized ionization gas. Nitrogen is the ionization gas in the preferred embodiment. The ionized gas molecules are directed by an electric field to the dielectric material where they transfer their charge as they strike the dielectric material. The gas is ionized with a high voltage anode with a potential between 3.5 and 7 KV. The gas ions are directed to the surface of the dielectric by the cathode 150 and the dual focusing grid 140. In addition, the dielectric material is moved at a constant rate over the cathode 150 and under the dual focusing grid 140 to ensure that the charge is distributed uniformly over the surface of the dielectric. Actually, the charge will only be uniform if the dielectric it free from defects, since defects will cause the electric field to become distorted and the charge to be unevenly distributed permitting the defects to be identified. FIG. 6A is a top view of a silicon wafer 200. FIG. 6B is a cross section view of a wafer 200 having a substrate 210 and a dielectric layer 201. The positive charge on the dielectric 201 is located at the exterior surface 202. The negative charge on the interior surface of the dielectric is drawn from the cathode 150 through the silver paint in notch 203 and the substrate 210.

In the preferred embodiment of step 30, the wafer is first placed inside the ionization chamber 112 and moved to the start position as illustrated in FIG. 7. The wafer is allowed to cool in the presence of nitrogen after being heated in step 20 of FIG. 5 to drive off any water. After the wafer 200 has cooled, a motor driving the slide is activated and then the high voltage power supply connected to the anode is activated. FIGS. 8A-D are graphs of the high voltage and time required to depost a charge of a particular voltage on the surface of the dielectric as a function of dielectric thickness. In the preferred embodiment, charge is deposited on the surface of the dielectric until a potential is developed which is typically from less than one volt per cm$^2$ for 100 angstrom oxides to greater than 90 volts per cm$^2$ for 20,000 angstroms 5 and 15 volts/cm$^2$. The resolution of the present invention may be adjusted by varying the potential resulting from the charge deposited on the surface of the dielectric. For example, referring to FIG. 8A, to place a 5 volt/cm$^2$ charge on the surface of a perfect dielectric with a thickness of 500 angstroms, the wafer needs to be exposed to 5.2 kV for 9.5 seconds. During the 9.5 seconds, the wafer is moved along the cathode under the dual focusing grid by the wafer carrier 250 until it reaches the end of the ionization chamber 112. The velocity of the wafer carrier 250 is adjusted so that the wafer travels the entire length of the ionization chamber 112 while charge is being deposited on the wafer. The velocity of the wafer carrier 250 is controlled by varying the drive voltage of the linear drive system motor. Just before the wafer reaches the end of the ionization chamber 112, the high voltage power supply is turned off, but the wafer continues to move along the cathode until it reaches the ending position. FIG. 9 is a cross section view of an ionization unit with the wafer in the ending position. The wafer now has a uniform charge, except where there is a defect in the surface of the dielectric.

The next primary step in the method for detecting defects in a dielectric material is the step of depositing an indicator on the surface of the dielectric to identiy the location of defects in the dielectric material. This involves depositing negatively charged carbon particles onto the surface of the dielectric. The carbon particles must be deposited uniformly and repeatably on the surface of the dielectric without disturbing the charge on the surface of the dielectric and without leaving any rings.

The preferred embodiment of the present invention employs a technique of heavy vapor deposition. The dielectric material is slowly submerged upside down in a indicator bath held in a deposition unit, then slowly raised out of the indicator bath, and then held just above the surface of the indicator bath until the carrier of the indicator has evaporated. The dielectric material is then removed from the deposition unit where it may be analyzed.

Figure 10:
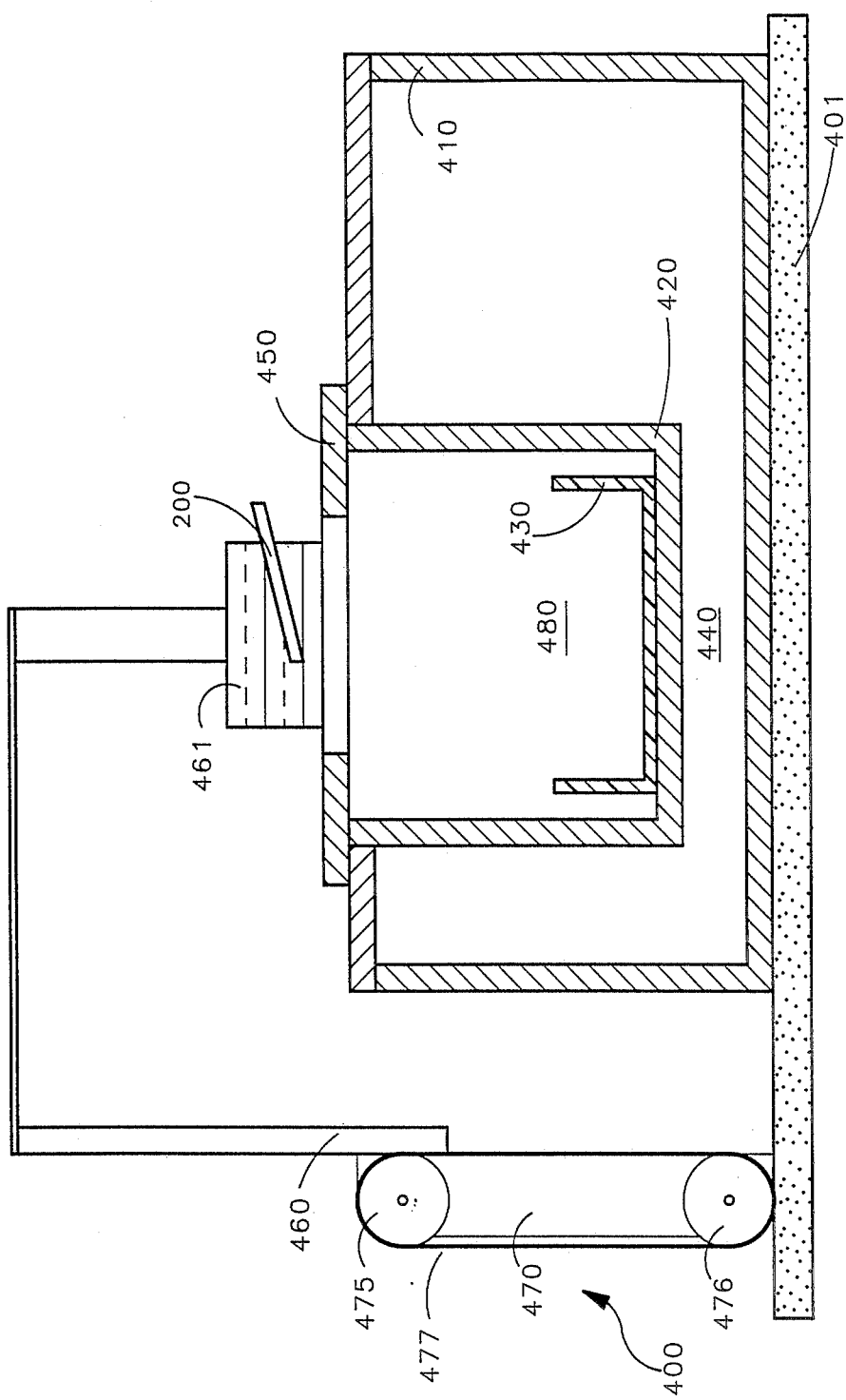
FIG. 10 is a cross section view of a heavy vapor deposition unit with the column positioning mechanism in the upper position.

FIG. 10 is a cross section veiw of a heavy vapor deposition unit with the column positioning mechanism in the upper position. A charged wafer 200 is inserted upside down into the wafer carrier 461. The wafer 200 is then lowered and submerged in the indicator bath for twenty-three seconds. At the time the wafer is being submerged the velocity of the meniscus across the surface of the dielectric both going in and coming back out of the indicator bath must be constant and as short as possible. The velocity of the meniscus is controlled by the angle of the wafer in the wafer carrier and the velocity of the column lift. The wafer 200 is angled in the wafer carrier 461 to prevent air from being trapped against the wafer as the wafer enters the indicator bath and to prevent the residual indicator bath from flowing back over the freshly coated area and disturbing the location of the indicator. While submerged in indicator bath, the positive charge on the surface of the dielectric attracts and holds the negatively charge carbon particles of the indicator to the surface of the dielectric material.

After the wafer has been submerged in the indicator bath for twenty-three seconds the column lifts the wafer 200 to a location just above the surface of the indicator bath. This area above the bath contains a heavy vapor of the carrier of the indicator, Freon TF in the preferred embodiment. It is the heavy vapor that retard evaporation of the indicator bath and permits the indicator to dry evenly on the surface of the wafer 200, drastically reducing the evaporation rings. For the controlled process of the preferred embodiment, the temperature in area 480 of the vessel must be a least zero degree Celsius or lower. At zero degrees Celsius, the wafer is held in the area immediately above the indicator bath for approximately two minutes to allow the carrier in the indicator bath to evaporated leaving only the indicator.

FIG. 11 is the top view of a wafer following the defect detection process illustrating the types of defects found on such a wafer. Defects take two primary forms. Defects with small diameters, less than 25 angstroms, appear as points or "omegas" 1010 under a microscope. These defects were undetectable with prior art techniques. These defects occur when the rate of charge deposited at the surface is greater than the charge removed through the defect in the dielectric to the cathode. The impedance and charge lifetime of such a defect may be calculated from the following equations:

$$R = pl/A \text{ and } C = eA/d$$

Where p is the ion conductivity in the presence of an electric field in ohms/centimeters, 1 is the thickness of the dielectric material in centimeters, A is the cross sectional area of the defect in square centimeters, d is the diameter of the oxide in centimeters, and e is the dielectric constant. For an oxide thickness of 470 angstroms and a defect of 25 angstroms, $p=10^{10}$ and $e=3.2$, the defect has an impedance of approximately $3*10^{18}$ ohms and a charge lifetime of approximately 59 minutes. Therefore, the charge will be remain on the surface and can be detected by the indicator. Although the impedance of the defect is large, the electric field is still sufficient to cause a large amount of charge to be drawn to the area. This charge, located virtually on top of the defect, give rise to the "omega" defect 1010.

Defects with larger diameters give rise to the "taurus" defect 1020 as shown in FIG. 10. For these defects, the electric field from the opposite side of the dielectric, which is referenced to ground, actually extends through the dielectric and conducts charge directly from the surface of the dielectric through the defect to the cathode. This leaves an area which is totally free of indicator immediately surrounding the defect. However, the same electric field with swallows the charge attracts additional charge to an area just outside this first area, generating a ring like appearance with identifies the larger "taurus" type defect.

These defects appear on a background of lightly deposited indicator. The deposit is so light and thin that the underlying circuitry may easily be seen. This light deposit of indicator corresponds to the uniform charge which is deposited in the absence of a defect. The amount of charge deposited is directly proportional to the thickness of the dielectric. Hence, the amount of indicator is directly proportional to the thickness of the dielectric. Therefore, integrated circuit structures, such as gate oxide for MOS devices with their thicker oxide layers will have less charge deposited and hence there will be less indicator deposited. This observation may be used to determine relative oxide thicknesses and establish the position and size of the underlying circuit elements.

The breakdown voltage of a dielectric material may be discovered using the present invention by repeatedly depositing a uniform charge with a predetermined potential, depositing the indicator, removing the indicator and then repeating the process with greater and greater potentials until the dielectric material breaks down and a defect discovered.

I claim:

1. A method for detecting defects in a dielectric material, said method comprising:
    bombarding a first side of the dielectric material with gas ions in order to place a uniform charge on the first side of said dielectric material;
    exposing a second side of the dielectric material to an electric potential opposite in charge to that of the gas ions;
    exposing the dielectric material to an indicator substance having an affinity for the charge delivered by the gas ions; and
    detecting the presence of defects in the dielectric material by accumulation of the indicator substance.

2. The process of claim 1 wherein the bombarding of the dielectric material takes place in an electric field which is nonstationary relative to the dielectric material.

3. A method for detecting defects in a dielectric material deposited on a metallic base, said method comprising:
    bombarding a first side of the dielectric material with inert gas ions in an electric field in order to place a uniform charge on the first side of siad dielectric material;
    exposing the metallic base to an electrical potential opposite in charge to that of the inert gas ions;
    exposing the dielectric material to an indicator substance having an affinity for the charge delivered by the inert gas ions; and
    detecting the presence of defects in the dielectric material by accumulation of the indicator substance.

4. The process of claim 3 wherein the bombarding of the dielectric material takes place in an electric field which is nonstationary relative to the dielectric material.

5. A method for detecting defects having diameters less than about 25 angstroms in a dielectric material deposited on a metallic base as part of an integrated circuit wafer, said method comprising:
    bombarding a first side of the dielectric material with positively charged nitrogen ions in an electric field in order to place a uniform positive charge of less than about 100 volts/cm$^2$ on the first side of said dielectric material,
    exposing the metallic base to an electrical potential opposite in charge to that of the positively charged nitrogen ions;
    immersing the dielectric material in a bath comprised of carbon particles and a carrier;
    evaporating the carrier in an atmosphere of the bath; and
    microscopically detecting the presence of defects having diameters less than about 25 angstroms as points of concentration of carbon particles on the first side of said dielectric material.

6. The process of claim 5 wherein the bombarding of the dielectric material takes place in an electric field which is nonstationary relative to the dielectric material.

7. A method for detecting defects in a dielectric material, said method comprising:
    bombarding a first side of the dielectric material with gas ions which are passed through a dual focusing grid in order to place a uniform charge on the first side of said dielectric material;
    exposing a second side of the dielectric material to an electric potential opposite in charge to that of the gas ions;
    exposing the dielectric material to an indicator substance having an affinity for charge delivered by the gas ions; and
    detecting the presence of defects in the dielectric material by accumulation of the indicator substance.

8. The process of claim 7 wherein the bombarding of the dielectric material takes place in an electric field which is nonstationary relative to the dielectric material.

9. A method for detecting defects in a dielectric material deposited on a metallic base, said method comprising:
    bombarding a first side of the dielectric material with inert gas ions which are passed through a dual focusing grid in order to place a uniform charge on the first side of the dielectric material;
    exposing the metallic base to an electrical potential opposite in charge to that of the inert gas ions;

exposing the dielectric material to an indicator substance having an affinity for the charge delivered by the inert gas ions; and detecting the presence of defects in the dielectric material by accumulation of the indicator substance.

10. The process of claim 9 wherein the bombarding of the dielectric material takes place in an electric field which is nonstationary relative to the dielectric material.

11. A method for detecting defects having diameters less than about 25 angstroms in a dielectric material deposited on a metallic base as part of an integrated circuit wafer, said method comprising:

bombarding a first side of a dielectric material with positively charged nitrogen ions which are passed through a dual focusing grid in order to place a uniform positive charge of less than 100 volts/cm$^2$ on the first side of the dielectric material;

exposing an opposite side of the dielectric material to an electric potential opposite in charge to that of the positively charged nitrogen ions;

immersing the dielectric material in a bath comprised of carbon particles and a carrier;

evaporating the carrier in an atmosphere of the bath; and microscopically detecting the presence of defects having diameters less than about 25 angstroms as points of carbon particle accumulation on the surface of the dielectric material.

12. The process of claim 11 wherein the bombarding of the dielectric material takes place in an electric field which is nonstationary relative to the dielectric material.

13. An apparatus for placing a uniform electric charge on a surface of a dielectric material wherein said apparatus comprises:

a gas ionization chamber having an inlet and an outlet for a gas to be ionized in said chamber;

an anode located within the chamber and electrically connected to a voltage source capable of ionizing a gas introduced into said chamber;

a cathode located within the chamber and electrically connected to a first surface of a dielectric material workpiece and to a ground potential in order to: (1) electrically interact with the anode and thereby create an electrical field which is capable of ionizing gas molecules in the chamber and bombarding said ions against a second surface of the dielectric material workpiece which is located in a region between the anode and the cathode and (2) ground the first surface of the dielectric material workpiece;

a gas capable of being ionized in the electrical field in said chamber and whose ions are capable of being bombarded against the second surface of the dielectric material workpiece;

a holding means for holding the dielectric material workpiece to be bombarded with gas ions;

a grid, located between the anode and the dielectric material workpiece, and having a potential lower than that of the anode.

14. The apparatus of claim 13 which further comprises means for moving the dielectric material workpiece relative to the electric field in the ionization chamber in laminer flow.

15. The apparatus of claim 13 which further comprises means for depositing an indicator substance on the ion bombarded second surface of the dielectric material.

16. The apparatus of claim 13 which further comprises means for circulating the gas through the chamber.

17. The apparatus of claim 13 wherein the grid further comprises a first layer of wire and a second layer of wire offset from the first layer of wire.

18. A method for determining a breakdown voltage of a dielectric material, said method comprising:

placing a first uniform charge on a first surface of a dielectric material workpiece by bombarding said first surface of the dielectric material with gas ions;

exposing a second side of the dielectric material to an electric potential opposite in charge to that of the gas ions;

exposing the dielectric material to an indicator substance having an affinity for the charge delivered by the gas ions and serving to identify the general location where a breakdown voltage was exceeded, removing the indicator;

placing a second uniform change on the first surface of the dielectric material workpiece which is greater than the first uniform charge; and depositing the indicator on the first surface of the dielectric material in order to identify a location where the breakdown voltage was exceeded.

* * * * *

UNITED STATES PATENT AND TRADEMARK OFFICE
CERTIFICATE OF CORRECTION

PATENT NO. : 4,803,435

DATED : February 7, 1989

INVENTOR(S) : Louis Thomas Mills

It is certified that error appears in the above-identified patent and that said Letters Patent is hereby corrected as shown below:

Column 1, line 54, should read between "dielectric." and "Defects"
 -- A light uniform charge is deposited by the present invention over the surface of the dielectric --;

Column 2, line 22, "any" should read -- this --;

Column 3, line 20, "theunit" should read -- the unit --;

Column 3, line 38, "delivery" should read -- deliver --;

Column 3, line 47, "embodimnet" should read -- embodiment --;

Column 4, line 2, "cathode.150." should read -- cathode 150. --;

Column 4, line 66, "dielectricis" should read -- dielectric is --;

Column 4, line 68, "and teh" should read -- and the --;

Column 5, line 15, "attached" should read -- attaches --;

Column 5, line 57, "240" should read -- 420 --;

Column 6, line 50, "sstep", should read -- step --;

UNITED STATES PATENT AND TRADEMARK OFFICE
CERTIFICATE OF CORRECTION

PATENT NO. : 4,803,435

DATED : February 7, 1989

INVENTOR(S) : Louis Thomas Mills

It is certified that error appears in the above-identified patent and that said Letters Patent is hereby corrected as shown below:

Column 6, line 65, "thirds step" should read -- third step --;

Column 6, line 67, "inventio" should read -- invention --;

Column 7, line 35, "depost" should read -- deposit --;

Column 7, line 66, "identiy" should read -- identify --;

Column 8, line 33, "charge" should read -- charged --;

Column 10, line 3, "siad" should read -- said --;

Column 12, line 43, "change" should read -- charge --.

Signed and Sealed this

Fifth Day of December, 1989

*Attest:*

JEFFREY M. SAMUELS

*Attesting Officer*     *Acting Commissioner of Patents and Trademarks*